(12) United States Patent
Folden et al.

(10) Patent No.: US 7,871,391 B2
(45) Date of Patent: Jan. 18, 2011

(54) EXTRACORPOREAL FLUID CIRCUIT

(75) Inventors: Thomas Irvin Folden, Alamo, CA (US); Martin Joseph Crnkovich, Walnut Creek, CA (US); Christian Schlaeper, Concord, CA (US); Lynn Jensen, Syracuse, UT (US); Mohsen Reihanifam, Rancho Santa Fe, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 594 days.

(21) Appl. No.: 11/256,627

(22) Filed: Oct. 21, 2005

(65) Prior Publication Data

US 2007/0106198 A1    May 10, 2007

(51) Int. Cl.
*A61M 37/00* (2006.01)
(52) U.S. Cl. ..................... 604/6.09; 604/6.14
(58) Field of Classification Search ....... 604/4.01–6.16, 604/156, 317, 327, 67, 131, 149, 319–321, 604/322, 403–411; 422/44–48; 128/898, 128/24; 73/700, 706, 715; 600/485–488; 210/739, 741
See application file for complete search history.

(56) References Cited

U.S. PATENT DOCUMENTS

| | | | |
|---|---|---|---|
| 3,946,731 A | | 3/1976 | Lichtenstein |
| 3,985,135 A | | 10/1976 | Carpenter et al. |
| 4,026,669 A | | 5/1977 | Leonard et al. |
| 4,370,983 A | | 2/1983 | Lichtenstein |
| 4,643,713 A | | 2/1987 | Viitala |
| 4,662,906 A | * | 5/1987 | Matkovich et al. ........... 96/6 |
| 4,702,675 A | | 10/1987 | Aldrovandi et al. |
| 4,997,464 A | * | 3/1991 | Kopf ........................... 96/6 |
| 5,061,236 A | | 10/1991 | Sutherland et al. |
| 5,330,425 A | | 7/1994 | Utterberg |
| 5,441,636 A | | 8/1995 | Chevallet et al. |
| 5,578,070 A | | 11/1996 | Utterberg |
| 5,614,677 A | | 3/1997 | Wamsiedler et al. |
| 5,643,205 A | | 7/1997 | Utterberg |
| 5,849,065 A | | 12/1998 | Wojke |

(Continued)

FOREIGN PATENT DOCUMENTS

EP    0458041    11/1991

(Continued)

OTHER PUBLICATIONS

Gambro®, "Prismaflex™, Anticipating Critical Care needs and taking our innovative response . . . to new heights", © 2004, Gambro Inc., Lakewood, CO, 8 pp.

(Continued)

*Primary Examiner*—Leslie R Deak
*Assistant Examiner*—Philip R Wiest
(74) *Attorney, Agent, or Firm*—Fish & Richardson P.C.

(57) ABSTRACT

A chamber is described for use in an extracorporeal fluid system. The chamber has a bottom entry port and a bottom exit port. A microporous filter at the top of the chamber allows air in the fluid to vent from the chamber. In use, the chamber is filled with saline. Blood is then introduced into the chamber. A layer of saline is above a layer of blood in the chamber. The saline stagnates as the blood flows through the chamber. The saline keeps the blood from contacting the filter and depositing protein on the filter.

36 Claims, 9 Drawing Sheets

U.S. PATENT DOCUMENTS

| | | | |
|---|---|---|---|
| 5,928,177 | A | 7/1999 | Brugger et al. |
| 5,989,423 | A | 11/1999 | Kamen et al. |
| 6,179,801 | B1 | 1/2001 | Holmes et al. |
| 6,196,987 | B1 | 3/2001 | Holmes et al. |
| 6,200,287 | B1 | 3/2001 | Keller et al. |
| 6,231,537 | B1 | 5/2001 | Holmes et al. |
| 6,234,989 | B1 | 5/2001 | Brierton et al. |
| 6,280,406 | B1 | 8/2001 | Dolecek et al. |
| 6,337,049 | B1 * | 1/2002 | Tamari ............... 422/44 |
| 6,361,518 | B1 | 3/2002 | Brierton et al. |
| 6,383,158 | B1 * | 5/2002 | Utterberg et al. ......... 604/4.01 |
| 6,409,696 | B1 | 6/2002 | Toavs et al. |
| 6,497,674 | B1 | 12/2002 | Steele et al. |
| 6,514,225 | B1 | 2/2003 | Utterberg et al. |
| 6,725,726 | B1 | 4/2004 | Adolfs et al. |
| 6,730,055 | B2 | 5/2004 | Bainbridge et al. |
| 6,755,801 | B2 | 6/2004 | Utterberg et al. |
| 6,764,460 | B2 | 7/2004 | Dolecek et al. |
| 6,790,195 | B2 | 9/2004 | Steele et al. |
| 6,852,090 | B2 | 2/2005 | Burbank et al. |
| 6,887,214 | B1 | 5/2005 | Levin et al. |
| 7,021,148 | B2 | 4/2006 | Kuhn et al. |
| 7,115,107 | B2 | 10/2006 | Delnevo et al. |
| 7,517,387 | B2 * | 4/2009 | Chevallet et al. ............ 95/24 |
| 2002/0014462 | A1 | 2/2002 | Muller |
| 2002/0072718 | A1 | 6/2002 | Brugger et al. |
| 2004/0238416 | A1 | 12/2004 | Burbank et al. |
| 2005/0054968 | A1 | 3/2005 | Giannella |
| 2005/0230292 | A1 | 10/2005 | Beden et al. |
| 2007/0193940 | A1 | 8/2007 | Duchamp et al. |
| 2007/0269340 | A1 | 11/2007 | Dannenmaier et al. |

FOREIGN PATENT DOCUMENTS

| | | |
|---|---|---|
| EP | 0 728 509 | 8/1996 |
| EP | 0887100 | 12/1998 |
| EP | 1529545 | 5/2005 |
| WO | WO 9702056 | 1/1997 |
| WO | WO 0108722 | 2/2001 |
| WO | WO 0164312 | 9/2001 |
| WO | WO 2005/044341 | 5/2005 |
| WO | WO 2005077490 | 8/2005 |

OTHER PUBLICATIONS

Gambro®, "DEHP-Free Cartridge Blood Sets", © Nov. 2004, Gambro, Inc, Lakewood, CO, 4 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prisma® HF 1000, For Increased Filtration Capacity", © Aug. 2001, Gambro Renal Products, Inc., Lakewood, CO, 2 pp.

Manns, Markus et al., "The acu-men: A new device for continuous renal replacement therapy in acute renal failure," *Kidney International*, vol. 54, pp. 268-274, 1998.

International Search Report and Written Opinion; PCT/US06/36802; mailed May 8, 2008.

* cited by examiner

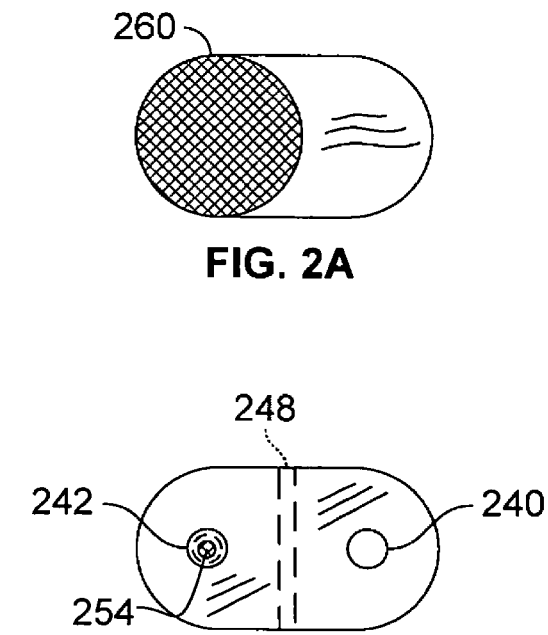
FIG. 2A
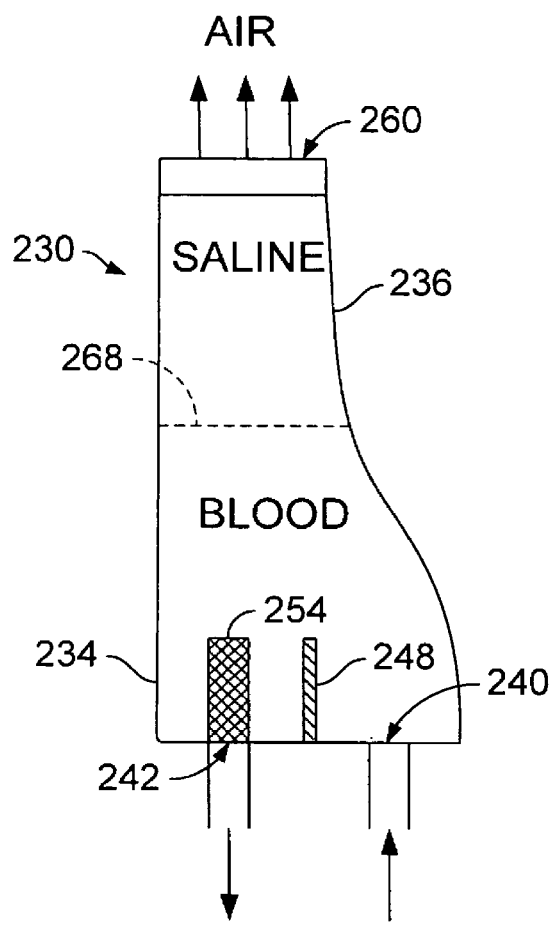
FIG. 2
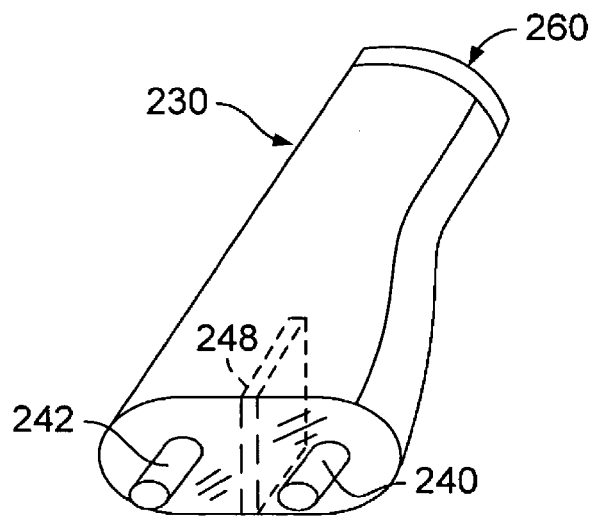
FIG. 2B
FIG. 2C

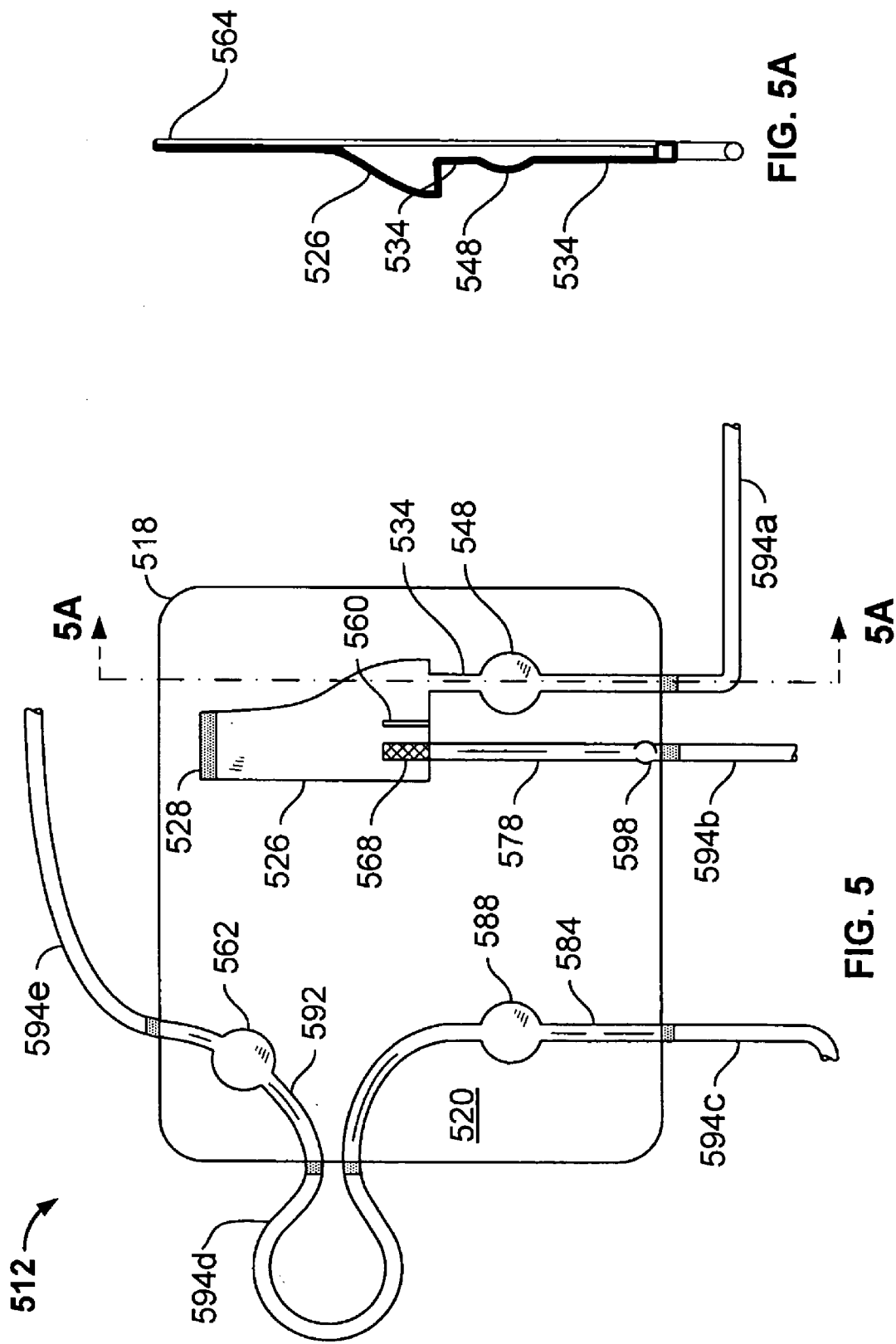

EXTRACORPOREAL FLUID CIRCUIT

BACKGROUND

This invention relates to extracorporeal liquid circuits. Hemodialysis removes toxic substances and metabolic wastes from the bloodstream using an extracorporeal circuit with components designed to perform ultrafiltration and diffusion on the blood. Before the blood is returned to the body, air bubbles are removed from the blood to prevent embolisms.

Referring to FIG. 1, a typical extracorporeal circuit 100 includes tubing through which the blood flows and components for filtering and performing dialysis on the blood. Blood flows from a patient 105 through arterial tubing 110. Blood drips into a drip chamber 115 where a sensor 125 in communication with air in the drip chamber 115 determines the pressure of the blood flow on the arterial side of the circuit 100. A pump 120 forces the blood to continue along the path through the circuit 100. A dialyzer 130 separates waste products from the blood.

After passing through the dialyzer 130, the blood flows through venous tubing 140 into a drip chamber 150. The drip chamber 150 can function as an air trap. Free gases in the blood may be able to escape into the drip chamber 150 before the blood continues to the patient. A sensor 170 is in communication with air in the drip chamber through tube 165. The sensor 170 can determine the pressure on the venous side of the circuit 100.

Heparin or drugs 160 can be added to the blood in the drip chamber 150. When blood is exposed to oxygen, the blood begins to clot. Even with the addition of heparin to the blood to prevent clots, some clotting may still occur. The drip chamber 150 includes a filter for preventing any clots from exiting the drip chamber 150 and entering the patient 105. The blood continues from the drip chamber through venous tubing 180 and through a bubble detector 175 before returning to the patient 105.

SUMMARY

An airless drip chamber is described that prevents blood in an extracorporeal blood circuit from being exposed to air. The airless chamber can be a stand-alone item, or incorporated into an integrated fluid circuit that also includes channels for directing blood to and from the drip chamber and pockets at which the pressure through the circuit can be measured. The integrated fluid circuit is a one-time-use disposable component that plugs into a hemodialysis machine or other extracorporeal fluid line.

In general, in one aspect, the invention is directed to an apparatus for removing air from a bodily liquid in extracorporeal circuitry. The apparatus has a vertical chamber having a bottom region and a top region and a pair of fluid entry and exit ports at or near the bottom region. A microporous filter is at or near the top region. Fluid passes through the vertical chamber from the entry port to the exit port so as to fill the vertical chamber with liquid while removing air from the chamber.

Implementations of the invention can include one or more of the following features. The microporous filter can include a hydrophobic material. The microporous filter can form at least a portion of a top surface of the vertical chamber. The fluid entry and exit ports can be in a bottom surface of the vertical chamber. The chamber can have a dam between the entry port and the exit port. The vertical chamber has a height sufficient to maintain an interface between a first liquid and a second liquid in the vertical chamber when the first and second liquids are miscible and the second liquid is flowing through the vertical chamber. The vertical chamber can have a bottom region that is wider than the top region. A clot filter can be positioned so that fluid passes through the clot filter prior to passing through the exit port. The microporous filter can fit within a housing connected to the top of the chamber. The bottom surface of the chamber can be sufficiently wide to accommodate an entry tube and an exit tube wherein the entry tube is connected to the entry port and the exit tube is connected to the exit port.

In another implementation, the invention can be directed to a method of removing air from a bodily liquid in extracorporeal circuitry. A first liquid is passed through an entry port into a bottom region of a vertical chamber, filling the chamber so that substantially no air remains in the chamber. A second liquid is passed through the entry port, thereby forcing a portion of the first liquid out of an exit port from the bottom region of the vertical chamber. A liquid-liquid interface forms between the first and second liquids. Gas bubbles in the second liquid are forced out of a top region of the vertical chamber through a microporous filter.

Implementations of the invention can include one or more of the following features. The first and second liquids can be miscible and the vertical chamber can be long enough to prevent the first and second liquids from mixing, because the first liquid stagnates. The method can include passing the second liquid through an exit port after air in the second liquid has escaped, thereby passing a substantially air-free second liquid through the exit port for delivery to a patient. The first liquid can be saline. The second liquid can be blood. The second liquid can be forced over a dam and out an exit port. The method can include passing the second liquid through a clot filter and an exit port.

In yet another implementation, the invention can be directed to an integrated fluid circuit component adapted to removably seat in a bodily liquid purification machine. The component includes a rigid body and a flexible backing. The rigid body has a substantially flat main portion and a plurality of recessed portions extending from the flat main portion. The flexible backing covers at least one of the of recessed portions. One of the recessed portions forms a vertical chamber. The vertical chamber has a microporous filter at or near a top region. One recessed portion forms a channel that is in fluid communication with a bottom region of the vertical chamber. Another recessed portion forms another channel in fluid communication with the bottom region of the vertical chamber.

Implementations of the invention can include one or more of the following features. The flexible backing can be sealed to the flat main portion of the rigid body, at least partially enclosing the recessed portions. One recessed portion can overlap one of the channels, where the recessed portion is wider than the channel. The channels can extend to the edge of the rigid body. The channels can be in fluid communication with tubes. The vertical chamber can include a clot filter adjacent to the second channel. The microporous filter can include a hydrophobic material. The vertical chamber can have a height sufficient to maintain an interface between a first liquid and a second liquid in the vertical chamber when the first and second liquids are miscible and the first liquid is stagnant as the second liquid flows through the vertical chamber. The component can include injection sites, such as neoprene gaskets. The component can include a rigid backing that backs at least the channels.

The invention can be implemented to realize one or more of the following advantages. Air may be prevented from contacting blood in the chamber. Preventing air from getting in the chamber may reduce the likelihood of clots forming in the blood. A hydrophobic microporous filter at the top of the chamber can allow any free gas or air that enters the chamber to escape. The chamber has a sufficient height so that a first liquid, such as saline, is located near a top of the chamber and blood is located near the bottom of the chamber and little mixing of the two liquids occurs. The length of the chamber is sufficient to allow the saline to stagnate and prevents mixing of the liquids, thereby preventing the blood from contacting the microporous filter. The saline can prevent most of the proteins in the blood from contacting the microporous filter. If protein accumulates on the microporous filter, the filter will wet and the filter's hydrophobic properties may be inhibited. That is, if the microporous filter wets, the filter may allow blood to escape from the chamber. Also, the filter can become inefficient at allowing air to pass through if protein collects on it. A dam in the chamber between the entry and exit ports diverts air bubbles toward the microporous filter. The microbubbles in the blood may then escape through the microporous filter rather than passing through the exit port. The system is free of a blood-air interface, which reduces the need for anti-coagulants. Reducing clot formation, reducing the need for anti-coagulant and reducing gas in the blood are desirable as safety measures for the patient undergoing hemodialysis.

Placing the components, such as a pocket for taking pressure measurements, channels for fluid flow and the airless chamber into a single integrated fluid circuit can eliminate multiple separate components. Fewer components are easier for an operator to work with and can reduce the risk of operator error. The integrated fluid circuit can have a rigid side that maintains the integrity of the components and a flexible side that allows for transducers to take measurements, such as pressure or temperature measurements. The flexible side can be sealed to the rigid side, potentially eliminating the need to construct a machine in which the integrated fluid circuit must be tightly held to the machine to seal the rigid and flexible sides together. Alternatively, the integrated fluid circuit can have two rigid sides with membranes only at critical locations.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a schematic cross-sectional view of an airless chamber.

FIG. 2A is a schematic top view of the airless chamber.

FIG. 2B is a schematic bottom view of the airless chamber.

FIG. 2C is a schematic perspective view of the airless chamber.

FIG. 5 is a plan view of an integrated extracorporeal circuit.

FIG. 5A is a cross sectional view of the integrated extracorporeal circuit of FIG. 5.

Like reference symbols in the various drawings indicate like elements.

DETAILED DESCRIPTION

Figure 1:
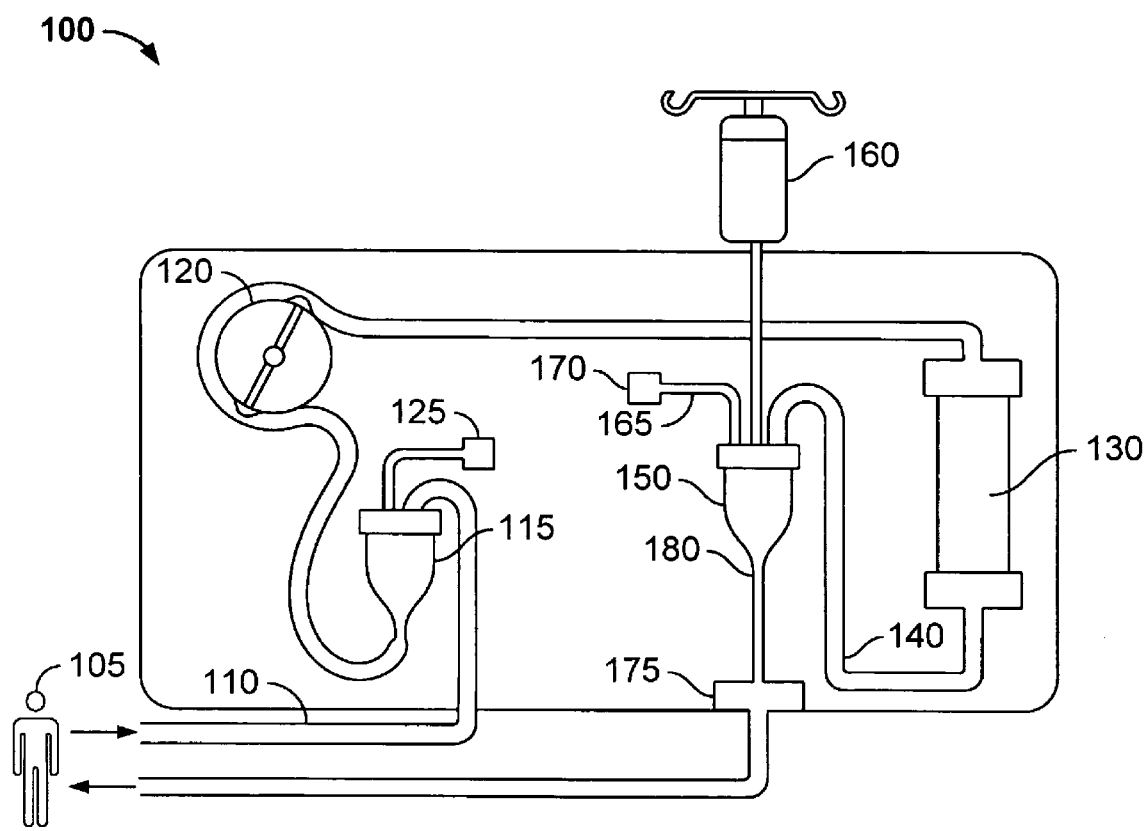
FIG. 1 is a schematic of a conventional hemodialysis system.
Figure 2D:
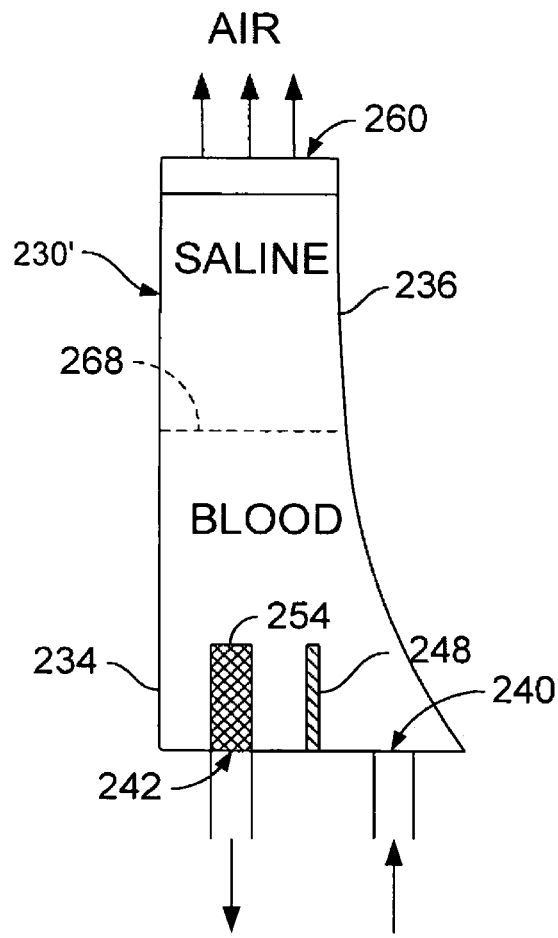
FIGS. 2D, 2E and 2F are each a schematic cross-sectional view of an airless chamber.
Figure 2E:
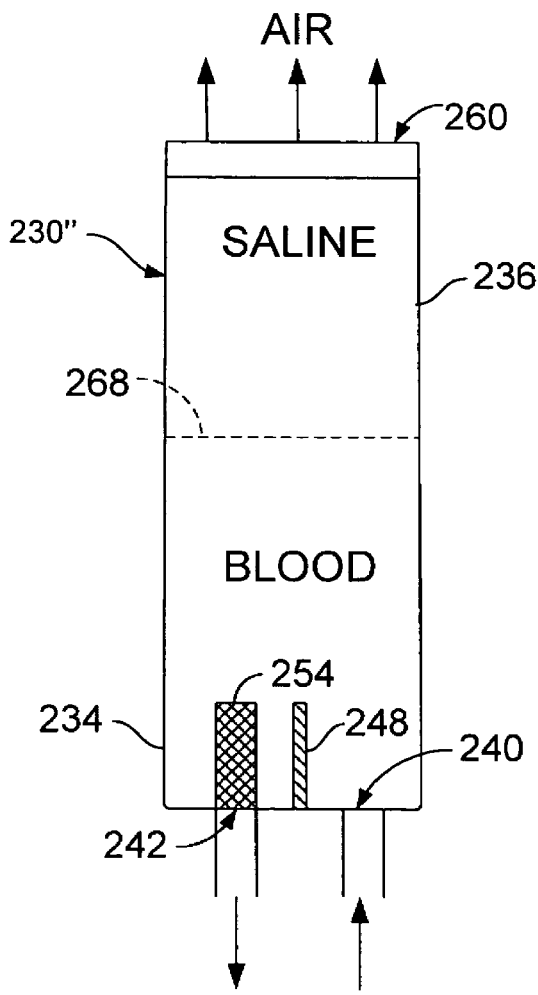
Figure 2F:
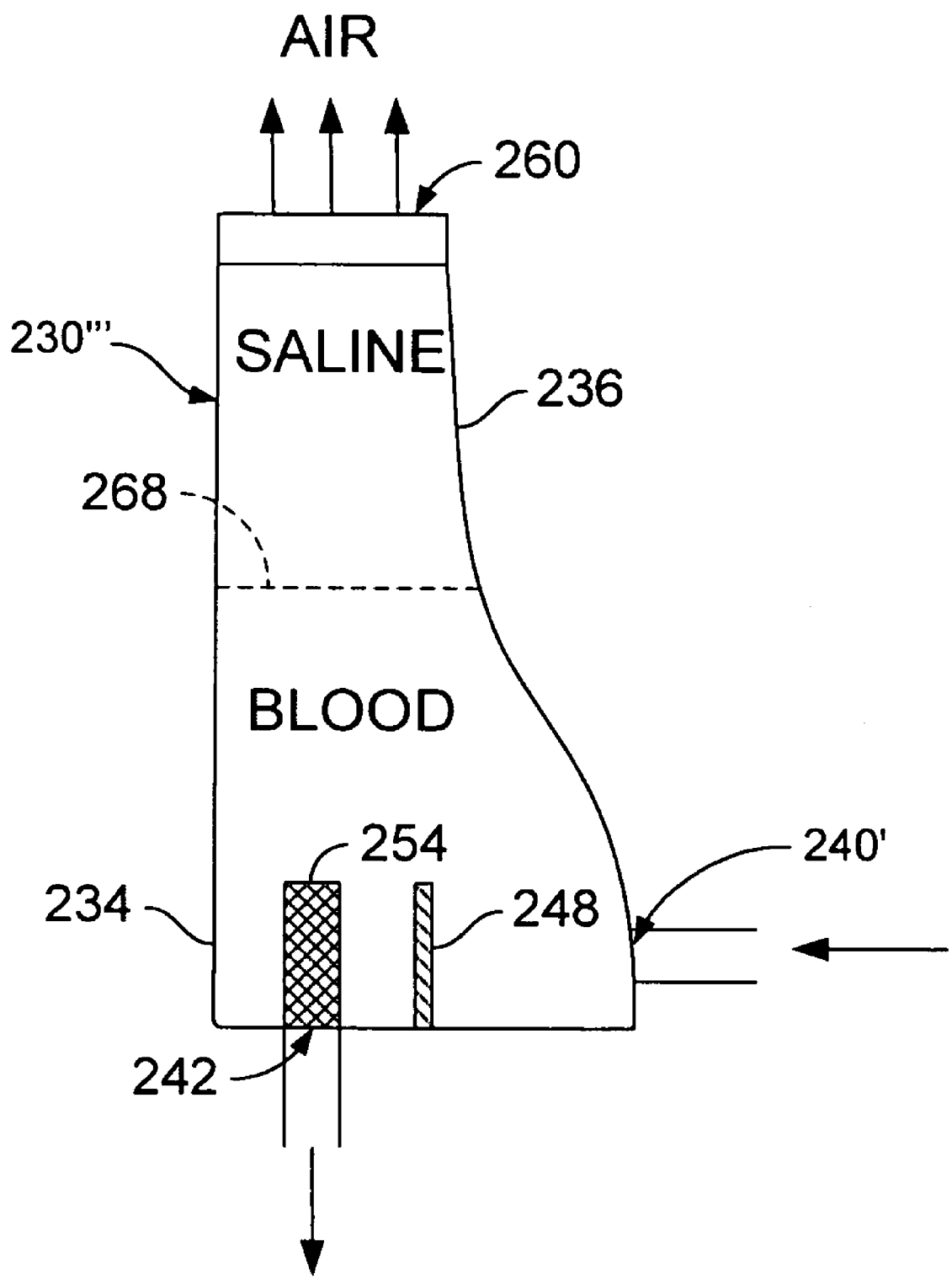

Referring to FIGS. 2, 2A, 2B and 2C, in some implementations, an airless chamber 230 is provided as a component of an extracorporeal fluid circuit. The chamber is substantially hollow for filling with a liquid. The chamber 230 can be used for removing gas from blood, but can also be used with a number of other fluids, such as bodily fluids, including plasma. The chamber 230 has a bottom region 234 and a top region 236, where the bottom and top are relative to the chamber's orientation during use. An entry port 240 and an exit port 242 are in the bottom region 234 of the chamber 230. In some implementations, the ports 240, 242 are located in a bottom surface of the chamber 230. In other implementations, as shown in FIG. 2F, at least one of the ports 240, 242 is located in a side surface of the chamber 230. In one implementation, a dam 248 is between the ports 240, 242. The dam 248 extends at least part way from one side wall to an opposite side wall. In one implementation, the dam 248 contacts each side wall so that all fluid entering entry port 240 flows over the top of the dam 248 before flowing out the exit port 242. In one implementation, a clot filter 254 is positioned adjacent to the exit port 242. Fluid flows through the clot filter 254 prior to flowing out of the exit port 242. In one implementation, the clot filter 245 has a porosity of between about 50-500 microns.

The ports 240, 242 are holes in the chamber which can be in fluid communication with tubular shaped extensions. The extensions are able to be connected to tubes, such as by pressure fitting or bonding. The extensions can be integrally formed with the chamber or subsequently attached to the chamber, such as by bonding or welding.

At the top region 236 of the chamber 230 is a microporous filter 260. The microporous filter 260 allows gas to vent from the chamber 230. Pores in the microporous filter 260 are small enough to keep foreign particles and organisms from entering the chamber 230 from the outside air. In one implementation, the filter 260 includes a hydrophobic material. A hydrophobic microporous filter keeps liquid from leaking out of the chamber 230 when the chamber 230 is substantially filled with liquid. A suitable filter has a pore size equal to or less than 0.45 microns, such as about 0.22 microns. The filter may be formed of polytetrafluoroethylene (PTFE) or any other suitable material.

When the chamber 230 is filled with blood, preventing the protein in the blood from accumulating on the filter 260 can maintain the hydrophobic characteristic of the filter 260. Whole blood can be kept from the filter by providing a barrier between the blood and the filter 260, such as a liquid barrier 268, as described further below. The height of the chamber 230 is sufficient to maintain this barrier 268 and prevents the liquid above the barrier 268 from substantially mixing with liquid below the barrier.

The shape of the chamber is approximately elongate. In some implementations, such as those shown in FIGS. 2 and 2D, the bottom region 234 of the chamber 230, 230' is wider than the top region 236, such that the chamber 230, 230' has a quasi-conical shape or a flare at the bottom. In some implementations, such as those shown in FIG. 2E, the top and bottom dimensions of the chamber 230" are approximately equal so that the chamber 230" has a rectangular or cylindrical shape. The bottom region 234 can also be narrower than the top region 236. If the ports 240, 242 are in the bottom surface of the chamber, the bottom surface has a sufficiently large dimension to accommodate the ports 240, 242 as well as any tubes coupled to the ports for directing fluid into and out of the chamber. For example, if the tubing has an outer diameter of 6.25 mm, the bottom surface is at least 12.5 mm wide. The exact dimensions of the chamber 230 are unimportant as long as the liquid barrier 268 is maintained, although the chamber 230 can be at least about two inches in height, preferably three to four inches.

The chamber is formed of a material suitable for medical devices, that is, a medical grade material. Plastics, such as polyvinylchloride, polycarbonate, polyolefins, polypropylene, polyethylene or other suitable medical grade plastic can be used because of their ease of manufacturing, ready availability and disposable nature. The chamber is formed, such as by molding, for example, extruding, blow molding or injection molding. The chamber can be formed of a transparent or clear material so that the liquid flowing through the chamber can be observed. The microporous filter at the top of chamber can be connected to the chamber in a number of ways. In one implementation, the filter fits into a cap-type housing and the housing is screwed or welded onto the top of the chamber. In another implementation, the microporous filter is adhesively attached to the chamber, such as with an epoxy. In yet another implementation, the microporous filter is co-molded during the injection molding process.

Figure 3:
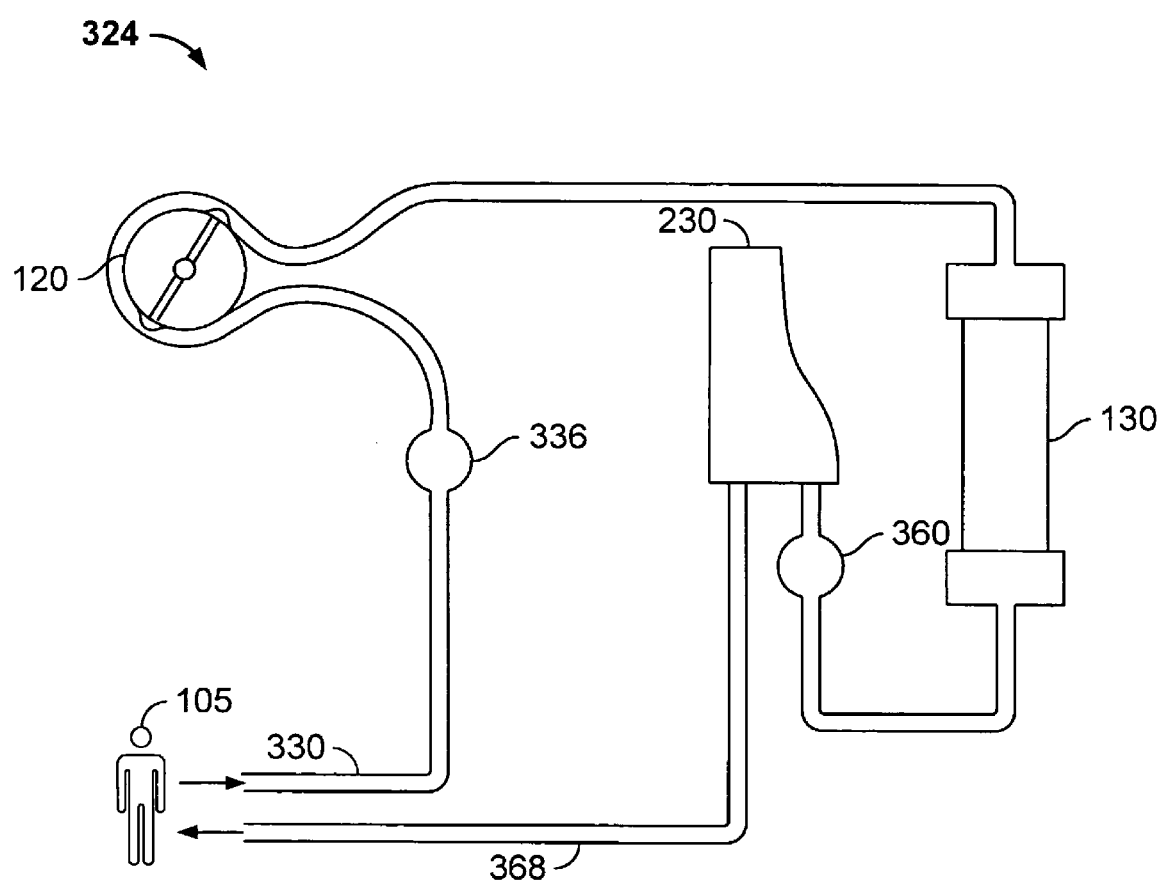
FIG. 3 is a schematic of an airless chamber in an extracorporeal circuit.
Figure 4:
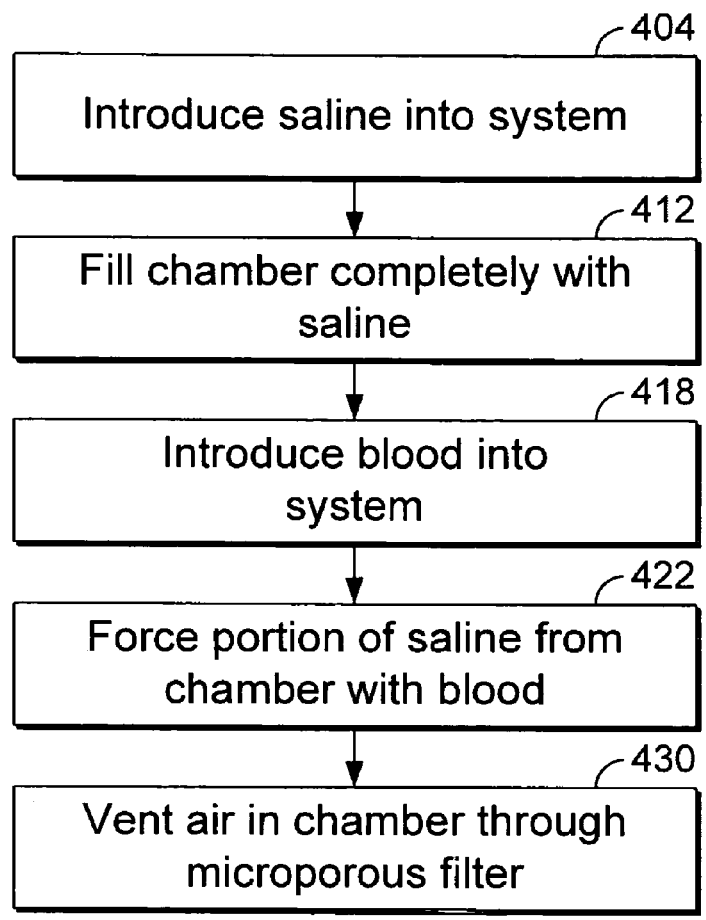
FIG. 4 is a flow diagram for using the airless chamber in an extracorporeal circuit.

Referring to FIGS. 3 and 4, the airless chamber 230 is in line in the extracorporeal fluid circuit of a system for fluid filtration and air removal. A first fluid that is compatible with the fluid to be filtered (the second fluid) is introduced into the system to prime the system (step 404). In hemodialysis, the first fluid is a blood compatible solution, such as saline. The saline flows through an arterial channel 330 to an arterial pressure sensor 336. The arterial pressure sensor 336 includes a transducer so that the pressure of the fluid flowing through the circuit 324 on the arterial side can be monitored. The saline then flows through a portion of the channel that abuts a pump 120, such as a peristaltic pump. The pump 120 forces the saline through the system 324. In some implementations, the pressure sensor 336 is after the pump 120. Alternatively, a arterial pressure sensor can be both before and after the pump 120. The saline then flows to the dialyzer 130 and then to a venous pressure sensor 360.

Next, the saline, or the first fluid, flows through the entry port of the chamber 230 and fills the chamber (step 412). To fill the chamber completely, venous channel 368 can be clamped to create a positive pressure once the saline is introduced into the chamber. Air is forced out the top of the chamber and through the microporous filter as saline fills the chamber. The saline contacts the filter and the chamber is substantially free of air once the chamber is completely filled. However, the saline does not exit through the filter, because the filter is hydrophobic. After the venous channel 368 is unclamped, the saline exits through the exit port of the chamber and out the venous channel 368.

Figure 4A:
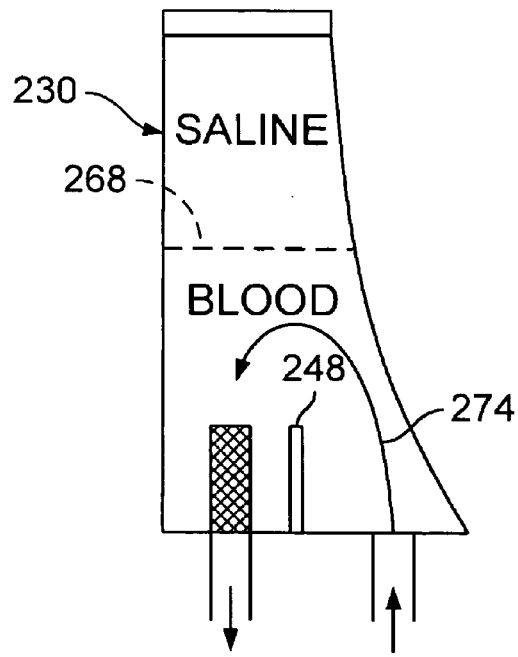
FIG. 4A is a schematic of the blood flow path through an airless chamber.

The second liquid, such as a bodily fluid, for example, blood, is then introduced into the system (step 418). The blood follows the same route as the saline and, for the most part, pushes the saline through the circuit. When the blood enters the chamber 230, the blood forces the saline at the bottom of the chamber through the exit port (step 422). However, the blood does not displace all of the saline within the chamber 230. Because of the height of the chamber 230, the blood enters the chamber 230 and only traverses part of the height of the chamber before flowing back down along flow path 274 to the exit port (as shown in the airless chamber formed of transparent material in FIG. 4A). An interface 268 between the saline and the blood delineates the furthest extent of most of the blood within the chamber 230. The interface 268 between the blood and saline can visually be observed and stretches across the entire width of the chamber. Because blood and saline are not immiscible, there is some amount of mixing between the two fluids around the interface 268.

The saline keeps the blood from contacting the filter. However, a percentage of blood can be present in the saline without hindering the operation of the system. That is, the saline need not be completely free from blood for the airless chamber to both allow gas to vent from the system and retain the liquid in the system. The solution that is mostly saline substantially protects the filter from becoming coated with protein. If the chamber is sufficiently elongated, the blood does not mix with the saline at the top portion of the chamber because the saline remains relatively stagnant as the blood flows through the chamber.

Any unbound gas, or air, that is in the blood, such as air that is introduced by the dialyzer or air that comes out of solution from the blood, rises as tiny air bubbles within the blood and saline until the air eventually vents out through the microporous filter (step 430). With a dam 248 inside of the chamber 230, the blood travels up and over the dam rather than straight across the bottom of the chamber out the exit port. By directing the flow of blood upwards, the blood with air is not able to flow in and directly back out of the chamber without flowing upwards to at least a height greater then the height of the dam. The surface area of the dam and the inner walls of the chamber enables air, including microbubbles, to separate from the blood and exit the fluid circuit through the microporous filter.

Throughout the circuit, the blood flows without there being a substantial air-blood interface. Although the blood does not come into contact with air and thus clotting is less likely to occur, the blood can pass through an optional filter in the chamber for added safety. In some implementations, after exiting the chamber, the blood passes by or through one or more sensors, such as temperature or air detecting sensors as an additional safety measure.

In one implementation, the airless chamber and one or more other components can be incorporated into an integrated fluid circuit. The integrated fluid circuit has the components described above, such as the airless chamber, formed together in one assembly or integrated molding rather than discrete separate or modular devices. The integrated fluid circuit is adapted to removably seat into a machine, such as a blood purification machine, like a hemodialysis machine. The integrated fluid circuit is similar to a cassette or cartridge, where an operator merely snaps the integrated fluid circuit into the machine and after just a few additional connections, begins operation.

Referring to FIG. 5, the integrated fluid circuit 512 has a rigid body 518 and a flexible backing (not shown). The rigid body has a substantially flat surface 520 with one or more concave (when viewed from the backside) portions or recessed portions protruding from a front surface of the body 518. The flexible backing can be applied so that the backing covers only the recessed portions or so that the backing covers more than just the recessed portions, up to all of the back surface of the rigid body.

The integrated fluid circuit has a recessed portion that serves as the airless chamber 526. As with the chamber described above, the airless chamber 526 includes a microporous filter 528 at a top region and optionally includes a dam 560 and a clot filter 568. A first channel 534 in rigid body 518 leads from an edge of the rigid body 518 to a bottom region of the airless chamber 526. Over one portion of the channel 534, a venous recess or pocket 548 is formed. The flexible backing backs the venous pocket 548. The venous pocket 548 is sized so that a transducer in the machine can measure the venous fluid pressure through the flexible backing. A second channel 578 extends from the outlet of the airless chamber 526 to an edge of the rigid body 518. The first and second channels extend to the same or different edges of the rigid body 518. The first channel 534 and second channel 578 are in fluid communication with the airless chamber 526.

In some implementations, a third channel 584 is formed in the rigid body 518. The third channel 584 is not in fluid communication with the first or second channels when the integrated fluid circuit is not in the machine or connected to a dialyzer. In some implementations, an arterial pocket 588 is formed along the third channel 584. The arterial fluid pressure can be measured through the flexible backing of the arterial pocket 588. One end of the third channel 584 extends to one edge of the rigid body 518 and the other end extends to the same or a different edge, as shown in FIG. 5.

Optionally, a fourth channel 592 extends across the rigid body 518. A post-pump arterial pocket 562 overlaps the fourth channel 592. In some implementations, additional recesses and channels are formed in the rigid body.

In some implementations, tubes 594a, 594b, 594c, 594d and 594e are connected to the rigid body 518, such as at the locations where the first, second, third and fourth channels extend to the edges. The tubes are connected to the rigid body using techniques known in the art. In some embodiments, the tubes fit into a pre-formed grooves in the rigid body 518. The tubes can be pressure fitted into the grooves. In other implementations, the tubes are clipped onto the rigid body 518. Optionally, at the end of the tubes 594a, 594b, 594c and 594e are fasteners for connecting the tubes to components of the machine, such as the dialyzer or to a patient. Tube 594d wraps around a peristaltic pump in the machine. Tubes 594a and 594e connect to a dialyzer. Tubes 594b and 594c connect to a patient.

Each of the recesses can protrude from the flat surface 520 to approximately the same distance. Alternatively, some of the recesses, such as the channels, may be shallower than other recesses, such as the airless chamber 526. Referring to FIG. 5A, a cross section of the integrated circuit 512 shows an outline of the pocket 548, channel 534 and part of chamber 526. The rigid body 520 can have an overall thickness of less than about 2 mm, such as less than about 1 mm. Flexible membrane 564 covers the back of the rigid body 520.

In some implementations, instead of one or more of the channels being formed in the rigid body 518, a tube is connected directly to a feature in the rigid body. For example, instead of forming second channel 578, tube 594b can be connected directly to the airless chamber 526.

In some implementations, the integrated circuit 512 has two rigid sides. The first rigid side is as described above. The second rigid side is substantially flat with openings located adjacent to the pockets formed in the first side. The openings are covered with a flexible membrane.

In some implementations, the integrated circuit 512 has posts that extend from one or more sides of the circuit. The posts can mate with recesses in the machine, ensuring correct registration of the integrated circuit 512 with components, such as sensors, in the machine. In some implementations, the integrated circuit 512 has latches, clips or other such device for registering the integrated circuit 512 with the machine and locking the integrated circuit 512 in place.

The machine can have a mechanism that holds the integrated circuit in place. The mechanism can comprise a door, a locking device or a suction device for holding the integrated circuit in tight contact with the machine. When the integrated circuit is seated in the machine, pressure transducers interface with the flexible backing to directly measure the fluid pressure at each of the corresponding locations. Holding the integrated circuit in contact with the machine allows the pressure transducers to sense flow through the circuit. Once the integrated fluid circuit is plugged into the machine and connected with the machine's components, an operator uses the integrated fluid circuit in a manner similar to the method of using the circuit chamber 230 described above.

As with the airless chamber 230, the rigid body 518 is constructed of a medical grade material. The flexible backing is constructed from a polymer that is flexible and suitable for medical use, such as an elastomer, including silicon elastomers. Other suitable materials include, high and low density poly ethylene, high and low density poly propylene, separately co-extruded mono layers or multiple layers of polyamides, nylons, silicones or other materials commonly known in the art for flexible applications. The backing is attached to the back of the rigid body 518, such as by laser, ultrasonic or RF welding or with an adhesive. In some implementations, the backing is attached so that the edge of each recess is sealed to the backing. Alternatively, the backing is attached only at the edge of the rigid body. If the backing does not seal the recesses from the flat portions, the machine into which the integrated fluid circuit seats is constructed to apply sufficient pressure to keep the fluid flowing through the circuit from leaking out of the recesses and between the backing and the flat surface 520. In the back of the rigid portion 518, ridges can be formed which surround the recesses. The ridges can aid in sealing the flexible membrane to the flat portion 518 when pressure is applied to the circuit.

In some implementations, injection sites 598 are formed at one or more of the recesses. The injection sites 598 can be used to inject drugs or solutions into the fluid. Suitable injection sites 598 are formed of neoprene gaskets into which a needle can be introduced and removed so that the gaskets do not leak or weep after the needle is removed.

Figure 6:
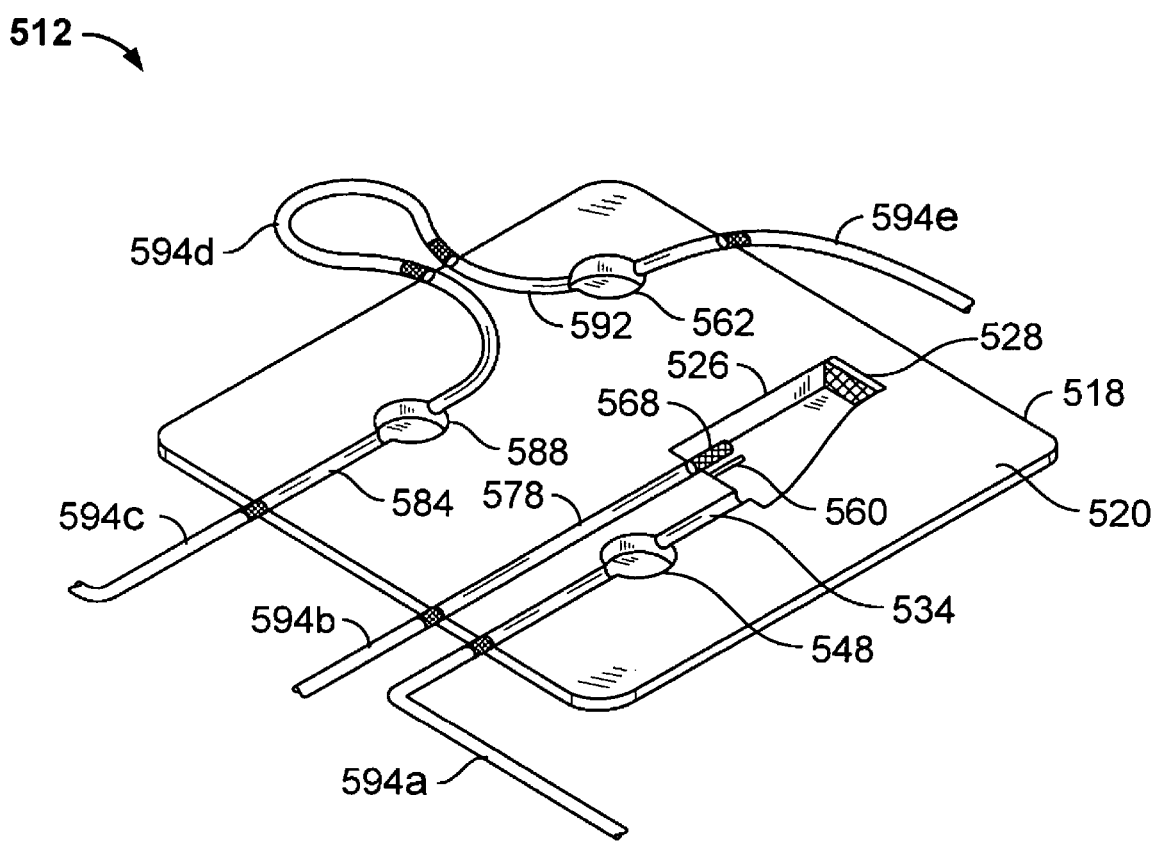
FIG. 6 is a perspective view of the integrated extracorporeal circuit.

FIG. 6 shows a perspective view of the integrated fluid circuit 512. As in FIG. 5, the flexible membrane has been removed from the integrated fluid circuit 512 to show the recesses.

Figure 7:
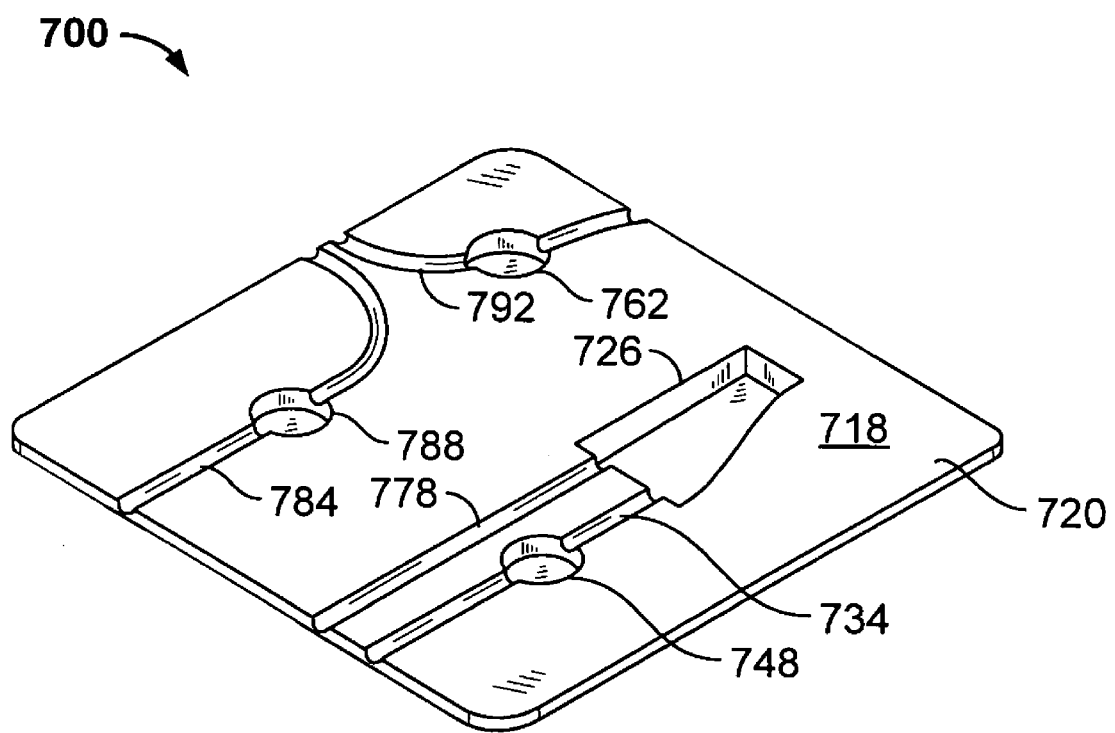
FIG. 7 is a perspective view of a bloodline guide for holding a tubing assembly, which is configured to retain the airless chamber shown in FIG. 3.

Referring to FIG. 7, a bloodline guide 700 is configured to hold a tubing assembly in proper alignment with respect to the components of the machine. The tubing assembly can include the airless chamber 230 and tubes, such as those shown in FIG. 3, and in some embodiments, includes components for allowing for detecting pressure within the guide. The bloodline guide 700 includes a rigid body 718 with a flat surface 720. A recess 726 is formed in the rigid body 718 that is configured to fit the airless chamber 230. Recesses 734, 778, 784 and 792 are sized for retaining tubing. Recesses 748, 762 and 788 are sized for retaining a component attached to or part of the tube where pressure can be monitored. Embodiments of the bloodline guide 700 include one or more of the recesses 726, 748, 734, 762, 778, 784, 788 and 792. In some implementations, the recesses 748, 762 and 788 are holes made in the rigid body 718.

In some implementations, the bloodline guide 700 includes a cover (not shown). The cover is a flat layer, such as a flat piece of plastic. The cover can be separate from the guide and can be temporarily attached to the bloodline guide, such as with clips. In some implementations, the cover extends from one side of the bloodline guide 700 with a hinge for bending the cover over the back of the bloodline guide 700, thereby covering the recesses. In some implementations, the cover has holes that align with the recesses 748, 762, 788. The holes can be open or covered with a membrane. The holes allow for a sensing device, such as a pressure transducer, to detect the pressure of liquid in the component in the recess.

In some implementations, the bloodline guide 700 includes clips, such as at an edge of the bloodline guide 700, for holding the tubes in the correct placement. Similar to the integrated circuit 500, the bloodline guide 700 can include posts for properly aligning the guide 500 with the machine. The bloodline guide 500 can be transparent, so that a user can see that the components and tubes in the guide are properly aligned when the guide is loaded into the machine.

Once the assembly including the airless chamber and tubes are placed in the bloodline guide 700, the bloodline guide 700 is loaded into the machine. In some implementations, the bloodline guide 700 includes posts, latches or other mechanism for ensuring proper registration with the machine.

Using the airless chambers described herein in an extra-corporeal blood circuit prevents air from contacting blood flowing through the circuit. Preventing air in the chamber can reduce the likelihood of forming clots in the blood. In the event that there is air in the blood before the blood exits the chamber, a hydrophobic microporous filter at the top of the chamber allows air that enters the chamber to escape. The filter is a part of or connected directly to the airless chamber. This allows the air to easily escape from the liquid filled chamber. Thus, lines need not be connected to the top of the chamber for withdrawing air from the circuit. Eliminating an air-blood interface increases the safety of the treatment for the patient. When clots form in the blood, the patient can be serious injured. Blood clots can cause thrombus, embolism, heart attack or stroke. Air bubbles in the blood also can injure the patient, such as by causing an air embolism. If the patient's blood never contacts air while flowing through the extra-corporeal circuit, no air will get into the blood, preventing air embolisms and blood clots caused by the treatment. Because the likelihood of clots is lessened, the amount of anticoagulant that is added to the blood can be decreased. Fewer additives in the blood during treatment are preferred because of the benefit to the patient's health.

The chamber is first filled with saline before being filled with blood. The chamber has a sufficient height so that after the saline and blood are introduced into the chamber, the saline is located near the top of the chamber and the blood is located near the bottom, and little mixing of the two liquids occurs. The saline prevents most of the proteins in the blood from contacting the filter at the top of the chamber. If protein accumulates on the filter, the filter's hydrophobic properties can be inhibited, that is, the filter can wet, allowing liquid to leak from inside the chamber to outside the chamber. Also, if protein collects on the filter, the filter becomes inefficient at allowing air to pass through. Thus, a sufficiently long chamber allows the saline to stagnate at the top, preventing protein from contacting the filter.

A dam in the chamber between the entry and exit ports may provide a surface for microbubbles to accumulate. The microbubbles in the blood may then escape through the chamber rather than passing through the exit port. Reducing clot formation and reducing gas in the blood is safer for the patient undergoing hemodialysis. The dam also forces the liquids up into the chamber so that the liquids, and any gases traveling with the liquids, are not immediately pushed out of the chamber before the gas can escape out to the top of the chamber.

Placing components, such as a pocket for taking pressure measurements, channels for fluid flow and the airless chamber, into a single integrated fluid circuit eliminates multiples separate components. Fewer components are easier for an operator to work with and reduce the risk of operator error. The integrated fluid circuit has a rigid side that maintains the integrity of the components, and flexible portions that allow for taking measurements, such as pressure or temperature measurements. Further, the pockets in the integrated circuit eliminate the need for pressure sensing lines in fluid communication with the top of the chamber.

A number of embodiments of the invention have been described. Nevertheless, it will be understood that various modifications may be made without departing from the spirit and scope of the invention. For example, the components described herein can be used with other fluids, such as plasma. Additionally, fluids other than saline can be used to prime the system. Accordingly, other embodiments are within the scope of the following claims.

What is claimed is:

1. An apparatus for removing air from a liquid in extracorporeal circuitry, the apparatus comprising:
   a vertical chamber having a bottom region and a top region and a fluid entry port and fluid exit port at or near the bottom region, the bottom region being flared such that the bottom region is wider than the top region;
   a microporous filter at or near the top region such that liquid can be passed through the vertical chamber from the entry port to the exit port so as to fill the vertical chamber with the liquid while air exits the chamber via the microporous filter,
   wherein the exit port is substantially vertically aligned with the filter during use, the entry port is horizontally offset from the filter during use, the vertical chamber has a height sufficient to allow a first liquid in the top region of the vertical chamber to remain substantially stagnant as a portion of a second liquid in the bottom region of the vertical chamber flows through the vertical chamber from the fluid entry port to the fluid exit port such that an interface between the first liquid in the top region of the vertical chamber and the second liquid in the bottom region of the vertical chamber is maintained as the portion of the second liquid flows through the vertical chamber from the fluid entry port to the fluid exit port, the first and second liquids are miscible, and the interface inhibits direct contact between the second liquid and the microporous filter.

2. The apparatus of claim 1, wherein the microporous filter includes a hydrophobic material.

3. The apparatus of claim 1, wherein the fluid entry and exit ports are in a bottom surface of the vertical chamber.

4. The apparatus of claim 1, wherein the microporous filter forms at least a portion of a top surface of the vertical chamber.

5. The apparatus of claim 1, further comprising a dam between the entry port and the exit port.

6. The apparatus of claim 5, wherein the dam is spaced apart from both the entry port and the exit port.

7. The apparatus of claim 5, wherein the dam extends upwardly from a bottom surface of the chamber, and wherein the dam extends at least part way from one side wall to an opposite side wall of the chamber.

8. The apparatus of claim 5, wherein the dam extends between and contacts opposing side walls of the chamber.

9. The apparatus of claim 1, further comprising a clot filter positioned in the bottom region of the chamber, the clot filter positioned so that the liquid passes through the clot filter prior to passing through the exit port.

10. The apparatus of claim 1, wherein the microporous filter fits within a housing connected at the top region of the chamber.

11. The apparatus of claim 9, wherein the clot filter is positioned adjacent to the exit port.

12. The apparatus of claim 1, wherein a bottom surface of the vertical chamber is sufficiently wide to accommodate an entry tube and an exit tube, the entry tube is connected to the entry port, and the exit tube is connected to the exit port.

13. The apparatus of claim 1, wherein the extracorporeal circuitry is dialysis extracorporeal circuitry.

14. The apparatus of claim 13, wherein the dialysis extracorporeal circuitry is hemodialysis extracorporeal circuitry.

15. The apparatus of claim 1, wherein the fluid entry port is horizontally offset from the top region of the chamber during use.

16. The apparatus of claim 1, wherein the chamber has a height of about three inches to about four inches.

17. A method of removing air from a liquid in extracorporeal circuitry, the method comprising:
 passing a first liquid through an entry port into a bottom region of a vertical chamber, filling the chamber so that substantially no air remains in the chamber;
 passing a second liquid through the entry port into the bottom region of the vertical chamber, thereby forcing a portion of the first liquid out of an exit port from the bottom region of the vertical chamber and forming a liquid-liquid interface between the first and second liquids within the vertical chamber;
 passing a portion of the second liquid out of the exit port from the bottom region of the vertical chamber while maintaining the liquid-liquid interface; and
 allowing gas in the first liquid or second liquid to pass through a microporous filter at or near a top region of the vertical chamber, wherein the bottom region of the vertical chamber is flared such that the bottom region is wider than the top region, the exit port is substantially vertically aligned with the filter, and the entry port is horizontally offset from the filter.

18. The method of claim 17, wherein the second liquid is miscible with the first liquid and the vertical chamber is long enough to prevent the first and second liquids from mixing because the first liquid stagnates.

19. The method of claim 17 wherein the second liquid that is passed through the exit port is substantially air-free and is delivered to a patient.

20. The method of claim 17, wherein passing a first liquid through an entry port includes passing a blood-compatible component through the entry port.

21. The method of claim 17, wherein passing a first liquid through an entry port includes passing saline through the entry port.

22. The method of claim 21, wherein passing a second liquid through an entry port includes passing blood through the entry port.

23. The method of claim 17, further comprising:
 forcing the second liquid over a dam after passing the second liquid through the entry port; and
 passing the second liquid out the exit port after forcing the second liquid over the dam.

24. The method of claim 17, further comprising:
 passing the second liquid through a clot filter; and
 passing the second liquid through the exit port after passing the second liquid through the clot filter.

25. The method of claim 17, wherein the extracorporeal circuitry is dialysis extracorporeal circuitry.

26. The method of claim 25, wherein the dialysis extracorporeal circuitry is hemodialysis extracorporeal circuitry.

27. The method of claim 17, whereby any gas bubbles contained in the second liquid are forced out of the top region of the vertical chamber through the microporous filter.

28. The method of claim 17, wherein the first liquid in the top region of the vertical chamber remains substantially stagnant as the portion of the second liquid flows through the bottom region of the vertical chamber from the entry port to the exit port such that an interface between the first and second liquids is maintained as the second liquid flows through the vertical chamber from the entry port to the exit port.

29. The method of claim 17, wherein the fluid entry port is horizontally offset from the top region of the chamber.

30. The method of claim 17, wherein the chamber has a height of about three inches to about four inches.

31. An air removal apparatus, comprising:
 a housing defining an elongate chamber having a top region and a flared bottom region that is wider than the top region, wherein a bottom surface of the housing defines an entry port and an exit port; and
 a filter in fluid communication with the elongate chamber, the filter configured to permit air to pass therethrough while substantially preventing liquid from passing therethrough,
 wherein the exit port is substantially vertically aligned with the filter during use, the entry port is horizontally offset from the filter during use, and the elongate chamber has a height sufficient to allow a first liquid in the top region of the elongate chamber to remain substantially stagnant as a portion of blood in the bottom region of the elongate chamber flows through the elongate chamber from the entry port to the exit port such that an interface between the first liquid in the top region of the elongate chamber and the blood in the bottom region of the elongate chamber is maintained while the portion of the blood flows through the chamber from the fluid entry port to the fluid exit port.

32. The air removal apparatus of claim 31, wherein the entry port is horizontally offset from the top region of the chamber during use.

33. An air removal apparatus, comprising:
 a housing defining an elongate chamber having a top region and a flared bottom region that is wider than the top region, wherein a bottom surface of the housing defines an entry port and an exit port; and
 a filter in fluid communication with the elongate chamber, the filter configured to permit air to pass therethrough while substantially preventing liquid from passing therethrough,
 wherein the exit port is substantially vertically aligned with the filter during use, the entry port is horizontally offset from the filter during use, and the elongate chamber has a height sufficient to allow saline in the top region of the elongate chamber to remain substantially stagnant as a portion of blood in the bottom region of the elongate chamber flows through the elongate chamber from the entry port to the exit port such that an interface between the saline in the top region of the elongate chamber and the blood in the bottom region of the elongate chamber is maintained while the blood flows through the chamber from the fluid entry port to the fluid exit port.

34. The air removal apparatus of claim 33, wherein the entry port is horizontally offset from the top region of the chamber during use.

35. A blood delivery method, comprising:
   forming a blood/saline interface between blood in a bottom region of a chamber in an air removal apparatus and a saline in a top region of the chamber in the air removal apparatus;
   passing a portion of the blood through the bottom region of the chamber, the blood passing into the bottom region of the chamber via an entry port formed in a bottom portion of the air removal apparatus, and the blood passing out of the bottom region of the chamber via an exit port formed in the bottom portion of the air removal apparatus, wherein the saline in the top region of the chamber remains substantially stagnant as the blood passes through the bottom region of the chamber such that the blood/saline interface is maintained while the blood passes through the bottom region of the chamber; and
   allowing gas in the saline or blood to pass through a microporous filter at or near a top region of the chamber, wherein the bottom region of the chamber is flared such that the bottom region is wider than the top region, the exit port is substantially vertically aligned with the filter, and the entry port is horizontally offset from the filter.

36. The method of claim 35, wherein the entry port is horizontally offset from the top region of the chamber.

* * * * *

UNITED STATES PATENT AND TRADEMARK OFFICE
CERTIFICATE OF CORRECTION

PATENT NO.         : 7,871,391 B2                                   Page 1 of 1
APPLICATION NO.    : 11/256627
DATED              : January 18, 2011
INVENTOR(S)        : Thomas Irvin Folden It is certified that error appears in the above-identified patent and that said Letters Patent is hereby corrected as shown below:

Claim 35, column 13, line 7:
    after "apparatus and" delete "a".

Claim 35, column 13, line 10:
    delete "bottomiegion" and replace with --bottom region--.

Signed and Sealed this
Twenty-second Day of March, 2011

David J. Kappos
*Director of the United States Patent and Trademark Office*